(12) United States Patent
Abe et al.

(10) Patent No.: US 7,824,337 B2
(45) Date of Patent: Nov. 2, 2010

(54) ULTRASONIC IMAGE PROCESSING APPARATUS AND CONTROL PROGRAM FOR ULTRASONIC IMAGE PROCESSING APPARATUS

(75) Inventors: Yasuhiko Abe, Otawara (JP); Tetsuya Kawagishi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 66 days.

(21) Appl. No.: 11/534,116

(22) Filed: Sep. 21, 2006

(65) Prior Publication Data

US 2007/0167777 A1 Jul. 19, 2007

(30) Foreign Application Priority Data

Dec. 27, 2005 (JP) .............................. 2005-376261

(51) Int. Cl.
*A61B 8/00* (2006.01)
(52) U.S. Cl. ....................... 600/441; 600/437; 600/443; 600/450
(58) Field of Classification Search ................. 600/441, 600/437, 443, 450
See application file for complete search history.

(56) References Cited

U.S. PATENT DOCUMENTS

| | | | | |
|---|---|---|---|---|
| 5,456,255 A | * | 10/1995 | Abe et al. | 600/443 |
| 5,622,174 A | * | 4/1997 | Yamazaki | 600/441 |
| 5,785,654 A | * | 7/1998 | Iinuma et al. | 600/441 |
| 6,053,869 A | * | 4/2000 | Kawagishi et al. | 600/443 |
| 6,638,221 B2 | * | 10/2003 | Abe et al. | 600/437 |
| 6,884,216 B2 | * | 4/2005 | Abe et al. | 600/440 |
| 2001/0034485 A1 | * | 10/2001 | Kawagishi et al. | 600/443 |
| 2003/0013963 A1 | * | 1/2003 | Bjaerum et al. | 600/443 |
| 2003/0171668 A1 | * | 9/2003 | Tsujino et al. | 600/407 |
| 2005/0085729 A1 | * | 4/2005 | Abe | 600/450 |
| 2006/0036172 A1 | | 2/2006 | Abe | |

FOREIGN PATENT DOCUMENTS

| | | |
|---|---|---|
| JP | 10-262970 | 10/1998 |
| JP | 3187008 | 5/2001 |
| JP | 2006-289067 | 10/2006 |

* cited by examiner

*Primary Examiner*—Brian Casler
*Assistant Examiner*—Peter Luong
(74) *Attorney, Agent, or Firm*—Oblon, Spivak, McClelland, Maier & Neustadt, L.L.P.

(57) ABSTRACT

Motion information of a tissue at a plurality of positions in a subject to be examined which is obtained by transmission/reception of an ultrasonic wave is acquired. This information includes, for example, a quantitative value associated with the strain of the tissue in the subject or a quantitative value associated with a displacement in the subject. A predetermined motion timing of the subject is calculated on the basis of the motion information of the tissue. A first image for indicating the motion timings of the tissue at a plurality of positions in the subject is generated.

20 Claims, 10 Drawing Sheets

| | Displacement | Strain |
|---|---|---|
| Short axis | Thickness change (+) | Thickness change (+) |
| Long axis | Longitudinal change (+) | Longitudinal change (−) |

ULTRASONIC IMAGE PROCESSING APPARATUS AND CONTROL PROGRAM FOR ULTRASONIC IMAGE PROCESSING APPARATUS

CROSS-REFERENCE TO RELATED APPLICATIONS

This application is based upon and claims the benefit of priority from prior Japanese Patent Application No. 2005-376261, filed Dec. 27, 2005, the entire contents of which are incorporated herein by reference.

BACKGROUND OF THE INVENTION

1. Field of the Invention

The present invention relates to an ultrasonic image processing apparatus which generates an image indicating the motion information of a subject to be examined on the basis of echo information obtained by transmitting/receiving ultrasonic waves to/from the subject, and a control program for the ultrasonic image processing apparatus.

2. Description of the Related Art

There is known an ultrasonic diagnostic apparatus which scans the interior of a subject with ultrasonic waves and visualizes the interior of the subject on the basis of reception signals generated from reflected waves from the interior of the subject. This ultrasonic diagnostic apparatus transmits ultrasonic waves from an ultrasonic probe into a subject, and receives, by the ultrasonic probe, reflected waves generated in the subject owing to acoustic impedance mismatch, thereby generating reception signals. It is known that such an ultrasonic diagnostic apparatus is also useful for cardiac diagnosis. Above all, it is very useful for diagnosis to objectively and quantitatively evaluate the function of a living tissue such as cardiac muscle.

As a therapy which has recently attracted attention, the cardiac resynchronization therapy (CRT) for a patient with severe heart failure is available. Attempts have been made to use an ultrasonic diagnostic apparatus for quantitative evaluation to determine whether this cardiac resynchronization therapy can be applied and determine the effects of the therapy.

This cardiac resynchronization therapy will be briefly described below. Many patients with severe heart failure also have systolic dyssynchrony of cardiac wall motion. The heart moves owing to the conduction of electrical signals. Intraventricular conduction disturbance may occur in patients with severe heart failure. In intraventricular conduction disturbance, a shift may occur in the sequence of conduction of electrical signals which cause the cardiac muscle to move. Due to this shift, there may be a portion which conducts early and a portion which conducts late in the cardiac ventricle which should conduct an electrical signal almost simultaneously. As a result, dyssynchrony occurs in the contraction of the cardiac wall, and blood cannot be sufficiently pumped out, resulting in heart failure. The cardiac resynchronization therapy is applied to such disturbance to help the pumping function of the heart by adjusting the sequence of conduction of electrical signals to the heart by artificially outputting electrical signals. More specifically, this therapy is achieved by embedding a pacemaker under the skin of the chest.

Such cardiac resynchronization therapy has already been applied to many patients, and dramatic improvements in symptom have been confirmed. On the other hand, it has been confirmed that about 30% of all the patients as heart failure cases have exhibited no improvements in symptom even upon application of this cardiac resynchronization therapy. This is because it cannot be accurately determined whether the cause of a heart failure case is systolic dyssynchrony. An application criterion for the cardiac resynchronization therapy is that the QRS width of an electrocardiographic waveform is more than 130 msec, and the left ventricular ejection fraction (EF) is less than 35%. This criterion is, however, met by even patients who have heart failure but have no systolic dyssynchrony.

Under the circumstances, therefore, there has been developed a technique of extracting only systolic dyssynchrony by a quantitative evaluation method using an ultrasonic diagnostic apparatus. As such a technique, for example, the technique disclosed in Jpn. Pat. Appln. KOKAI Publication No. 10-262970 is known, which detects the motion velocity of the cardiac muscle (cardiac wall) and computes/analyzes the motion velocity. According to this technique, the peaks of changes with time, e.g., changes in motion velocity or displacement, at a plurality of regions of the cardiac muscle can be automatically detected. The times taken to reach these peaks from a predetermined cardiac phase are calculated, and an ultrasonic image of the cardiac muscle is colored in accordance with the calculated times. Outputting the motion state differences of the overall cardiac muscle as a color image makes it possible to visualize the differences in motion timing between the respective regions of the cardiac muscle.

The following problems, however, arise in the above conventional techniques. According to the technique disclosed in patent reference 1, the motion velocity of the cardiac muscle is computed/analyzed. However, since velocity is an instantaneous physical quantity, a change in myocardial velocity with time does not always have a peak only in accordance with the contraction state of the ventricle. In a heart failure case, in particular, it is known that the myocardial velocity has many peaks, because the cardiac muscle moves abnormally. That is, it is difficult to perform stable evaluation from a motion velocity to determine which peak is a peak indicating significant ventricular contraction.

Figure 12:
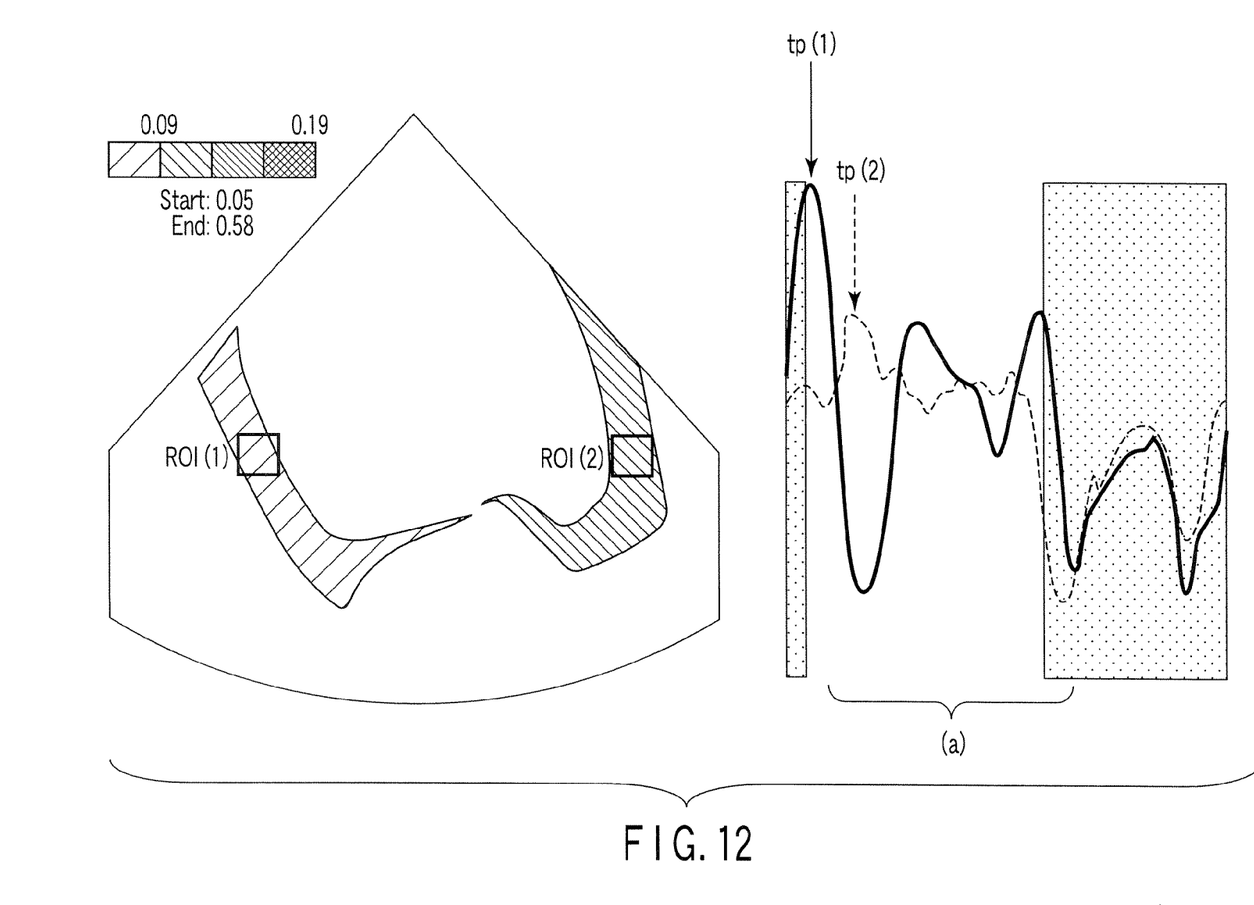
FIG. 12 is a view for explaining a conventional technique.
Figure 13:
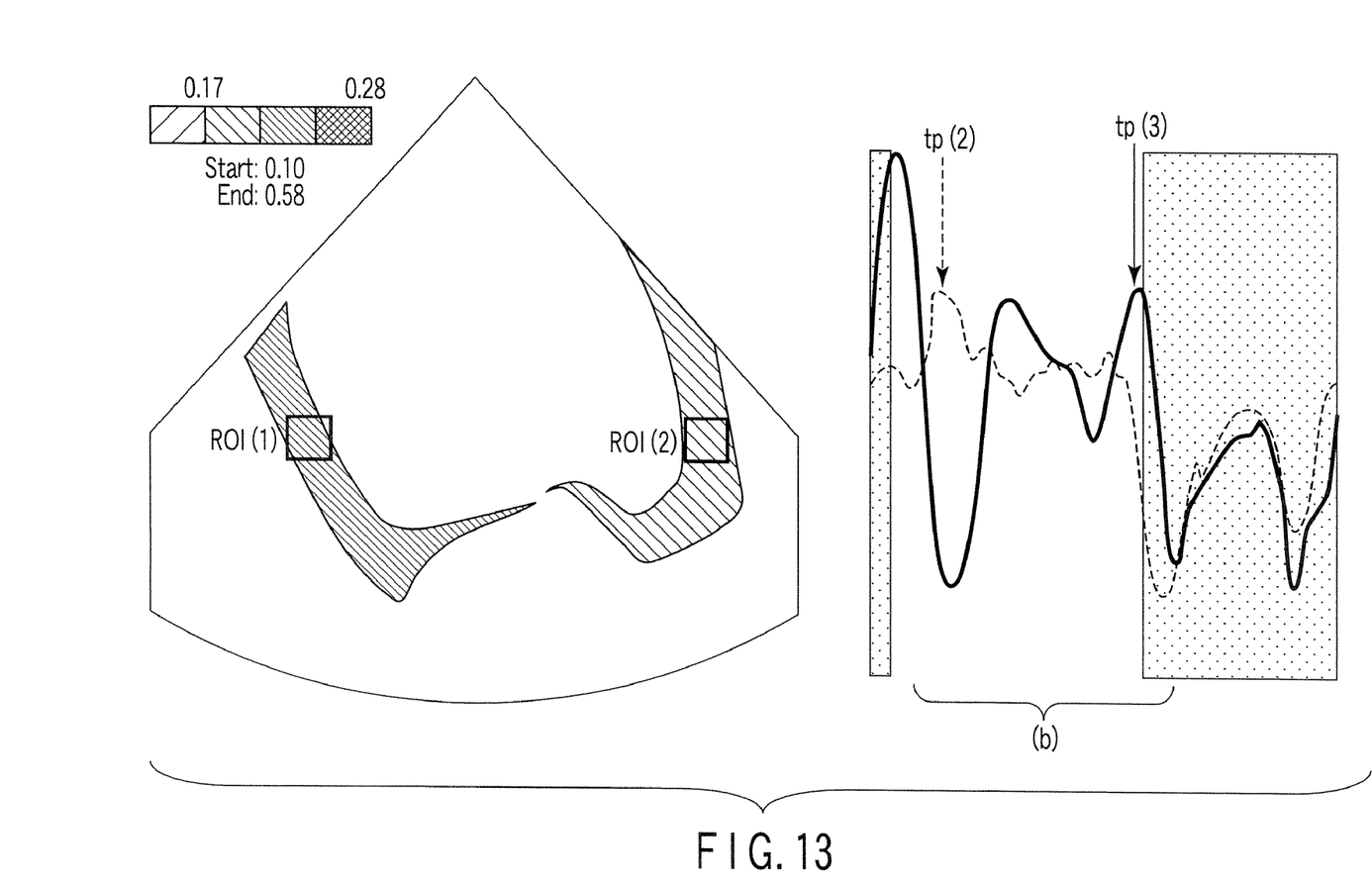
FIG. 13 is a view for explaining the conventional technique.

This relationship will be described concretely with reference to FIGS. 12 and 13. In each graph, the solid line represents a change in the velocity of a region ROI 1 designated on an ultrasonic image of a portion near the left ventricle with time, and the dotted line represents a change in the velocity of a region ROI 2 with time. Each graph indicates a change in velocity in one cardiac cycle and, more specifically, a change in velocity in the interval from early-systole to end-diastole which is delimited near an R wave. FIG. 12 shows a case wherein peak detection is performed in an area (a) including the early-systole interval. At this time, the peak of the motion velocity of the ROI 1 is detected at a position tp1, and the peak of the motion velocity of the ROI 2 is detected at a position tp2. If, however, peak detection is performed in an area (b) excluding the early-systole interval as shown in FIG. 13, the peak detection result totally differs from the above. Although the peak of the motion velocity of the ROI 2 is still detected at the position tp2, the peak of the motion velocity of the ROI 1 is detected at position tp3. The ultrasonic images in FIGS. 12 and 13 are shaded in accordance with the times taken to reach the peaks. In the case shown in FIG. 12, it is observed that the septum side contracts early, and the lateral wall side contracts late. In the case shown in FIG. 13, the opposite is observed.

According to the technique disclosed in patent reference 1, therefore, since the possibility of erroneously detecting a peak indicating significant contraction in a heart failure case is high, it is difficult to reliably detect systolic dyssynchrony.

BRIEF SUMMARY OF THE INVENTION

The present invention has been made in consideration of the above problems, and has as its object to provide a medical image processing apparatus which allows correct comprehension of the motion state of a tissue in a subject to be examined, and a control program for the medical image processing apparatus.

According to an aspect of the present invention, there is provided an ultrasonic image processing apparatus comprising a motion information computation unit which acquires motion information of a tissue at a plurality of positions in a subject to be examined which is obtained by transmission/reception of ultrasonic waves, a time computation unit which acquires a predetermined motion timing of the subject on the basis of the motion information of the tissue, and a display control unit which generates a first image indicating information associated with the predetermined motion timing.

According to another aspect of the present invention, there is provided an ultrasonic image processing method comprising acquiring motion information of a tissue at a plurality of positions in a subject to be examined which are obtained by transmission/reception of ultrasonic waves, acquiring a predetermined motion timing of the subject on the basis of the motion information of the tissue, and generating a first image for indicating information associated with the predetermined motion timing.

DETAILED DESCRIPTION OF THE INVENTION

An embodiment of the present invention will be described below. This embodiment will exemplify a case wherein the local motion of a cardiac muscle tissue of the heart as a target is evaluated by using a two-dimensional image.

(Arrangement)

Figure 1:
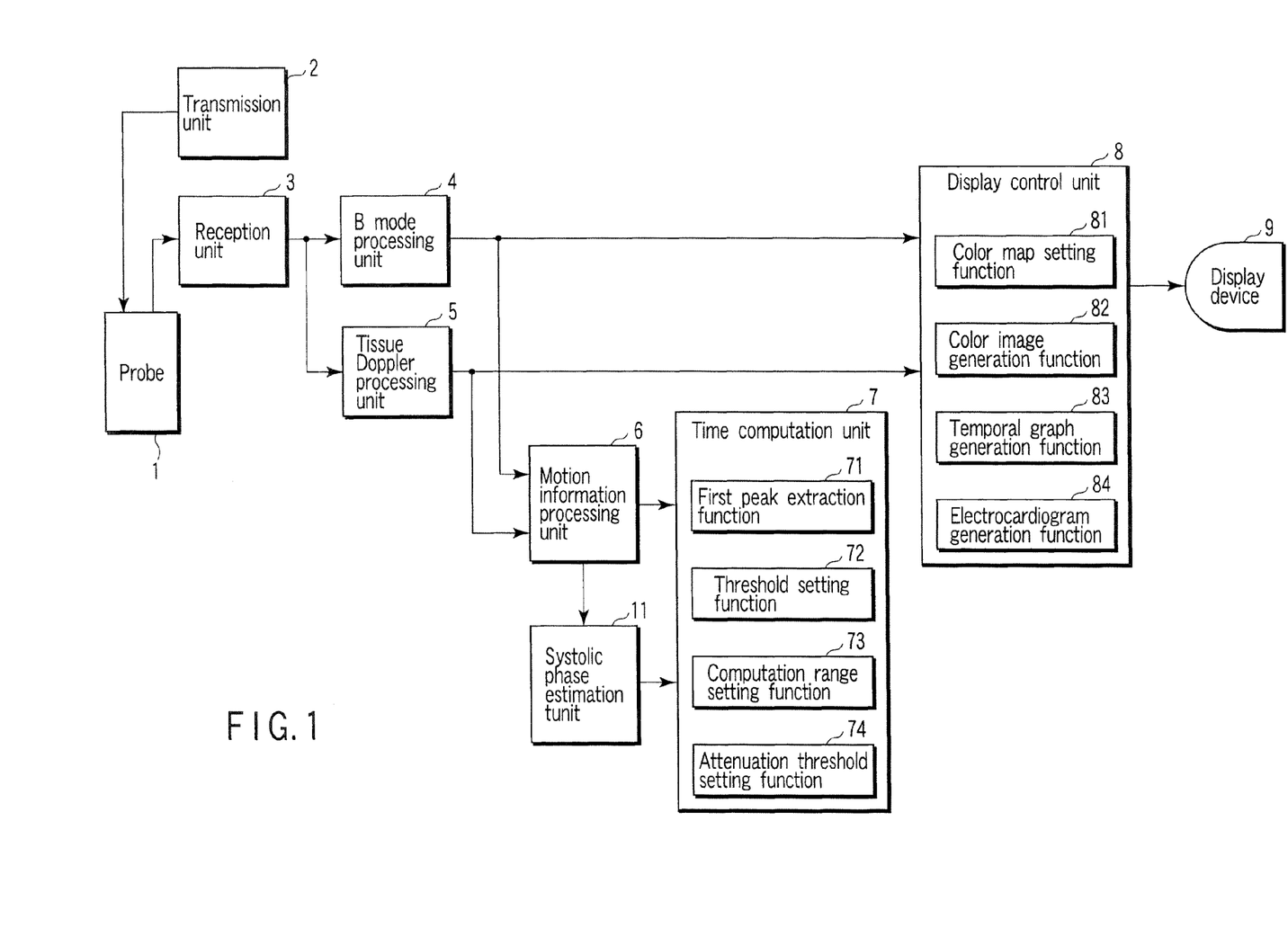
FIG. 1 is a block diagram showing the arrangement of an embodiment of the present invention.

FIG. 1 is a block diagram showing the arrangement of an ultrasonic image processing apparatus according to an embodiment of the present invention. An ultrasonic probe 1 includes an ultrasonic transducer array of a plurality of ultrasonic transducers which convert electrical signals into ultrasonic waves. Ultrasonic waves are transmitted/received to/from a subject by using this ultrasonic transducer array. Assume that in the first embodiment, the ultrasonic probe 1 is a sector probe targeted to the heart.

A transmission unit 2 generates driving signals for transmitting ultrasonic waves from the ultrasonic transducer array. The transmission unit 2 generates a driving signal having a predetermined delay characteristic for each transducer so as to form an ultrasonic beam toward a predetermined scan line.

A reception unit 3 generates an ultrasonic echo signal corresponding to a predetermined scan line by performing delay addition processing for the ultrasonic echo signal received by each ultrasonic transducer of the ultrasonic transducer array.

A B mode processing unit 4 generates a B mode signal corresponding to the amplitude intensity of an ultrasonic echo by performing envelope detection processing for the ultrasonic echo signal having undergone the delay addition processing. The B mode processing unit 4 also generates a B mode ultrasonic image representing a two-dimensional distribution associated with a predetermined slice of this B mode signal.

A tissue Doppler processing unit 5 performs quadrature detection processing, autocorrelation processing, and the like, and obtains a tissue Doppler signal corresponding to the velocity, variance, and power of a tissue moving in the subject on the basis of the Doppler shift component of the ultrasonic echo signal having undergone the delay addition processing. The tissue Doppler processing unit 5 generates two-dimensional distribution information associated with a predetermined slice of this velocity/variance/power value.

A motion information processing unit 6 executes each processing for the acquisition of motion information on the basis of the two-dimensional distribution information output from the tissue Doppler processing unit 5. More specifically, the motion information processing unit 6 computes motion information concerning a local displacement or strain by performing time integration processing using the local tissue velocity obtained from the two-dimensional distribution information, and provides the two-dimensional distribution information. In this case, a displacement is a value indicating how much the tissue in the subject has moved within an arbitrary period of time, and a strain is a value indicating how much the distance between two points on the tissue in the subject has changed within an arbitrary period of time.

Assume that in this case, the time integration processing for obtaining a displacement or a strain is performed in synchronism with a cardiac time phase. More specifically, assume that an electrocardiogram of the subject is acquired by an electrocardiogram unit (not shown), and a predetermined cardiac time phase (QRS wave) is specified from this electrocardiogram, and that the above time integration processing is reset at every cardiac phase. As a specific technique of acquiring such motion information, the technique disclosed in Jpn. Pat. Appln. KOKAI Publication No. 2002-272845 can be used.

Assume that such displacement or strain information is to be acquired upon tracking the position of a tissue. In this embodiment, the position of a tissue is tracked on the basis of tissue Doppler information. However, the present invention is not limited to this. The position of a tissue may be tracked by using B mode information.

In addition, when such motion information is acquired, angle correction may be performed. In general, Doppler information is information associated with motion along the scanning line direction. Therefore, when, for example, a left ventricular short axis image has been obtained, it is preferable that a strain or displacement associated with a change in the thickness of the cardiac muscle is be extracted upon angle correction based on a component toward the contraction center. If an apical image has been obtained, it is preferable that a strain or displacement associated with the expansion/contraction of the cardiac muscle in the longitudinal direction is extracted by adjusting a contact between a probe and an subject to be examined so as to detect a component in a direction along the endocardial surface.

A time computation unit 7 includes a first peak extraction function 71, threshold setting function 72, computation range setting function 73, and attenuation threshold setting function 74. The first peak extraction function 71 detects a time point at which a change in strain or displacement reaches its extreme value for the first time on the basis of the motion information acquired from the motion information processing unit 6. Note that, in the present embodiment, to simplify the explanation, an extreme value is a peak. The first peak extraction function 71 also calculates the time taken to reach the peak from a predetermined time point. By obtaining such a peak arrival time at each point within a designated range, the spatial distribution information of peak arrival times can be obtained. These computations are performed within the range set by the threshold setting function 72 or the computation range setting function 73, and a predetermined amount of attenuation is set as a condition for peak detection on the basis of the condition set by the attenuation threshold setting function 74. These functions will be described in detail later.

A display control unit 8 includes a color map setting function 81, color image generation function 82, temporal graph generation function 83, and electrocardiogram generation function 84. The color image generation function 82 generates a display image on the basis of the spatial distribution information of peak arrival times which is obtained by the time computation unit 7. The information of the peak arrival time at each point is color-converted on the basis of the settings of the color map setting function 81 to generate image data superimposed on a B mode image. The temporal graph generation function 83 displays a change in motion information concerning a strain or displacement in the ROI designated on an image in the form of a graph. The electrocardiogram generation function 84 generates the image data of an electrocardiogram of the subject through the electrocardiogram unit (not shown). Image data generated by the respective functions will be described later. A display device 9 displays the image data generated by the display control unit.

A systolic phase estimation unit 11 estimates an end-systolic phase or a delayed contraction phase. The assignment of color information to each peak arrival time is determined on the basis of this information so as to display systolic dyssynchrony more conspicuously. The display control unit 8 generates a color image on the basis of this assignment. A specific estimation method performed by the systolic phase estimation unit will be described in detail later.

Each component in this embodiment may be implemented as hardware such as a circuit board, or may be implemented as software. When each component is to be implemented as software, a program for implementing the function of each component is stored in a storage means such as a memory or hard disk. When these programs are loaded in the built-in CPU, operation based on the concept shown in FIG. 1 is performed.

(Operation)

Figure 2A:
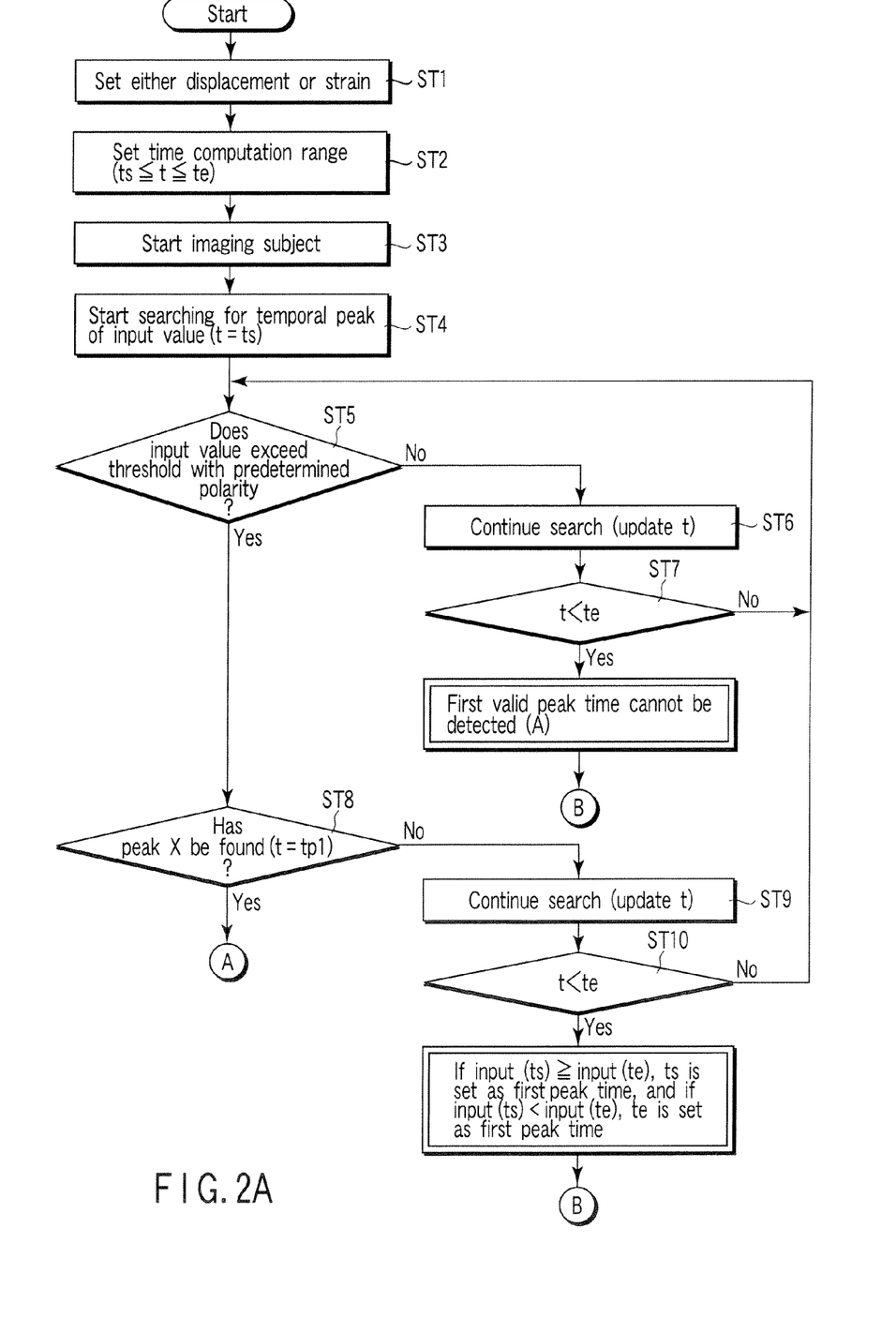
FIGS. 2A and 2B are flowcharts showing operation in the embodiment shown in FIG. 1.
Figure 2B:
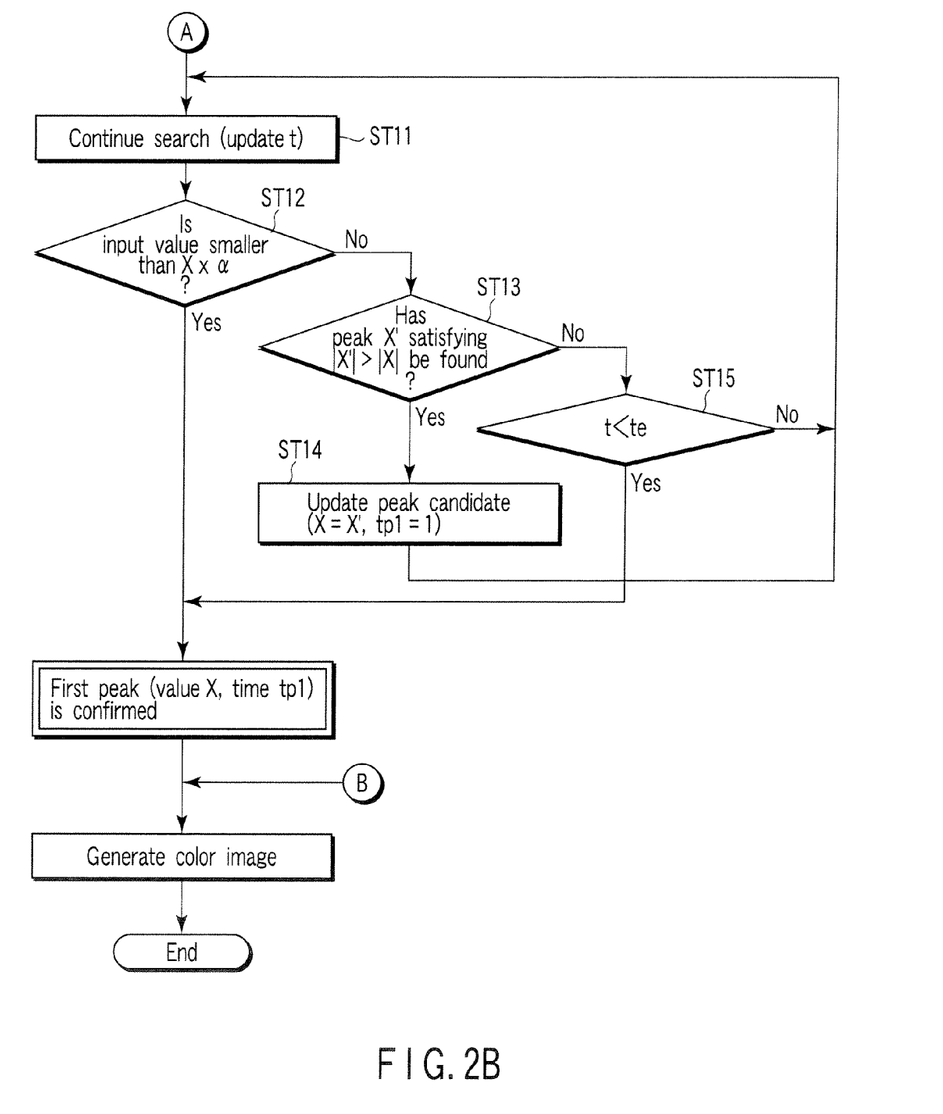

FIG. 2 is a flowchart showing the operation of an ultrasonic image processing apparatus according to this embodiment. The operation will be described in accordance with this flowchart. In this case, the operation of the time computation unit 7 which is a characteristic portion of this embodiment will be mainly described.

First of all, in step S1, motion information to be acquired by the motion information processing unit 6 is set. That is, the operator selects whether processing is performed on the basis of a displacement or a strain or whether ultrasonic waves are applied from the short axis direction or the long axis direction. The motion information processing unit 6 determines, in accordance with this setting, a specific direction component whose displacement or strain is to be acquired, and calculates a displacement or strain suitable for diagnosis by performing angle correction based on this direction component.

Figure 3:
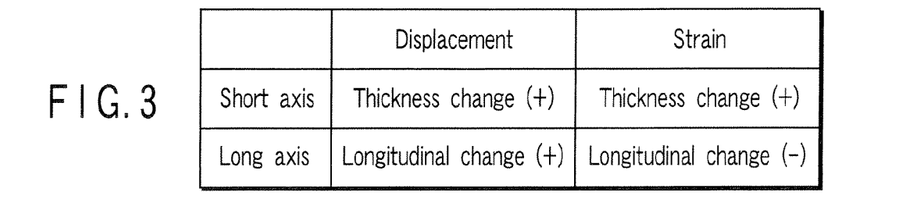
FIG. 3 is a view showing a list of pieces of motion information acquired in the embodiment in FIG. 1.
Figure 4:
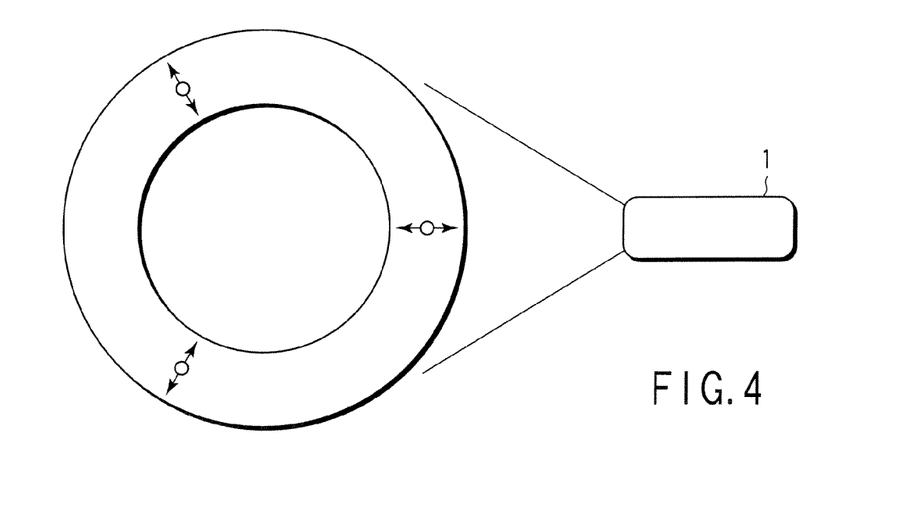
FIG. 4 is a schematic view for explaining angle correction to be performed when a displacement in a short axis image is acquired as motion information.
Figure 5:
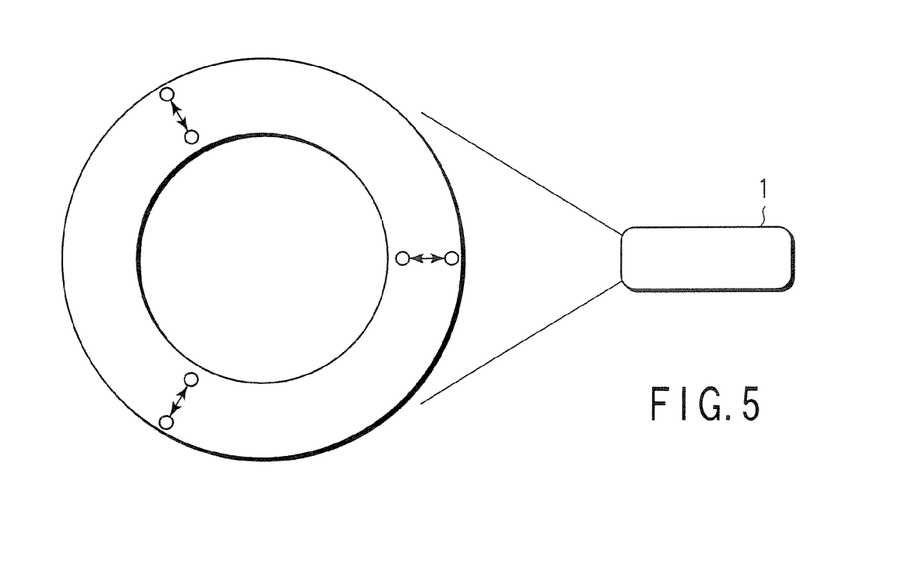
FIG. 5 is a schematic view for explaining angle correction to be performed when a strain in a short axis image is acquired as motion information.

FIG. 3 is a table showing the relationship between the above settings made by the operator and direction components whose displacements and strains are acquired. A case wherein a displacement on the short axis is selected will be described first. The thickness of the cardiac muscle at early-systole differs from that at end-systole. Since a short axis image is suitable for the observation of this change, angle correction is performed so as to calculate the displacement of the cardiac muscle in the thickness direction. More specifically, as shown in FIG. 4, a displacement in a direction toward the center point of the heart which is set on the basis of designation by the operator or automatic contour extraction is calculated at each point on the tissue. Referring to FIG. 4, each circle "○" indicates a tissue, and each arrow indicates a direction in which calculation is performed. As shown in FIG. 4, since the direction in which a displacement should be calculated and the application direction of ultrasonic waves from the ultrasonic probe 1 change at each point, correction is performed for such changes. Since the cardiac muscle is displaced toward the center as the heart contracts, the obtained value increases with the contraction. Referring to FIG. 3, "(+)" indicates a case wherein the value increases with contraction, and "(−)" indicates a case wherein the value decreases. When the strain of a short axis image is selected, a strain in a direction toward the center of the heart is obtained by correction based on an angle relationship like that shown in FIG. 5. Referring to FIG. 5, each circle "○" indicates a tissue, and a strain is obtained on the basis of the positional relationship between two circles "○" in the arrow directions. Since the thickness of the cardiac muscle increases as the heart contracts, the obtained value increases with the contraction.

Figure 6:
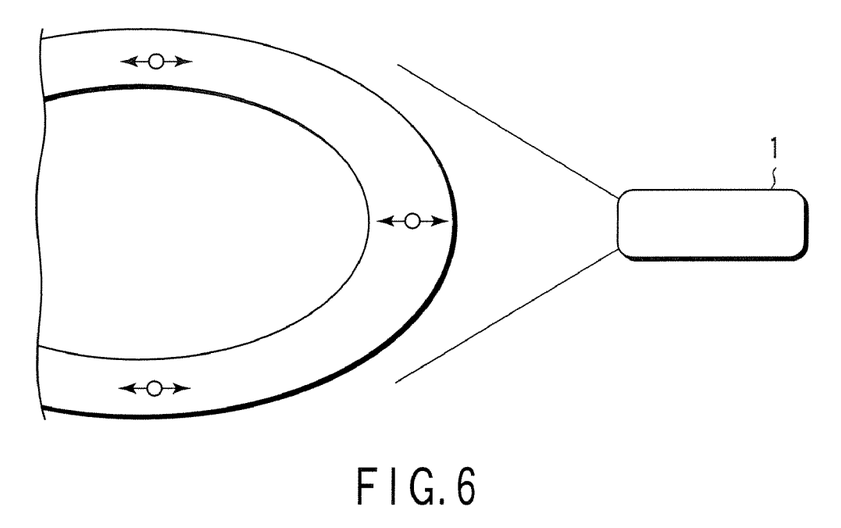
FIG. 6 is a schematic view for explaining angle correction to be performed when a displacement in a long axis image is acquired as motion information.
Figure 7:
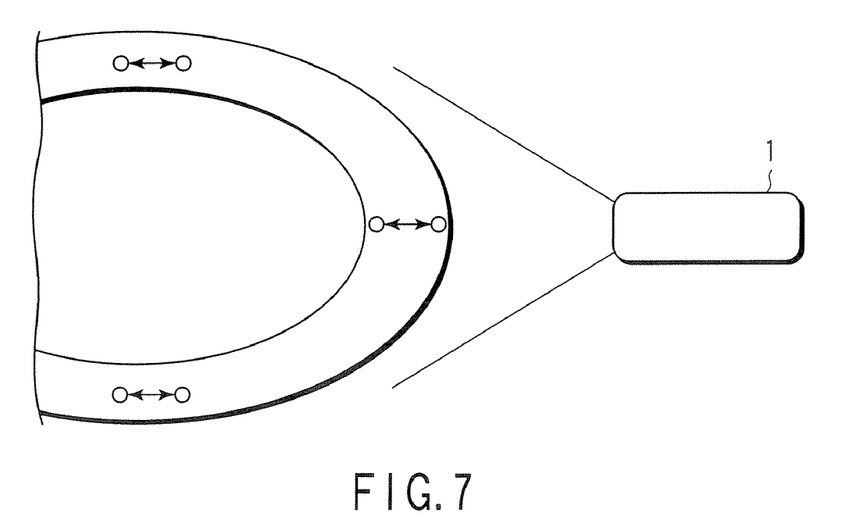
FIG. 7 is a schematic view for explaining angle correction to be performed when a strain in a long axis image is acquired as motion information.

A case wherein a displacement on the long axis is selected will be described. The heart contracts in the longitudinal direction (long axis direction). Since a long axis image is suitable for the observation of this change, a displacement in the longitudinal direction is calculated. More specifically, as shown in FIG. 6, a displacement in the longitudinal direction of the heart is calculated at each point on the tissue. Since the cardiac muscle is displaced in a direction against the probe as the heart contracts, if a direction toward the probe is regarded as a positive direction, the obtained value increases as the heart contracts. This applies to a case wherein a strain on a long axis image is selected. On the other hand, the strain of the heart in the longitudinal direction is obtained based on an angle relationship like that shown in FIG. 7.

In step S2, the computation range setting function 73 sets a time computation range. A time computation range is a time range in which the peak of a change in the above motion information concerning the strain or displacement with time is obtained. It is useful for diagnosis of systolic dyssynchrony to detect the differences between the contraction timings at the respective portions of the cardiac muscle within a contraction interval within one heartbeat. Therefore, a time computation range is adjusted within a contraction interval. More specifically, the operator sets the start and end points of a time computation range by moving a cursor on an electrocardiographic waveform or a temporal change graph of a strain or displacement in a designated area which is displayed on the display device 9. The computation range setting function 73 recognizes and stores them in a predetermined memory. As a concrete method of setting a time computation range, a method of inputting numerical values indicating a specific range of seconds from an R wave or inputting a value in a relative time unit with a time corresponding to one heartbeat being set as 1 may be used. A start point ts and end point te of a time computation range are determined in this manner, and a time computation range satisfying ts≦t≦te is set.

In step S3, the operator brings the ultrasonic probe 1 into contact with the subject to image the subject. The operator adjusts the position of the ultrasonic probe 1 so as to obtain a desired image while seeing a real-time image displayed on the display device 9. With this operation, imaging is started.

In step S4, the motion information concerning the displacement or strain of each imaged portion is set as an input value, and a search for the peak of this input value is started. The first peak extraction function 71 of the time computation unit 7 starts to search for a peak from the spatial distribution of motion information, of the motion information acquired from the motion information processing unit 6, which is acquired at a time point represented by t=ts within one predetermined heartbeat.

In step S5, the first peak extraction function 71 determines whether an input value at time $\underline{t}$ exceeds the threshold set by the threshold setting function 72. Motion information often has a plurality of relatively small peaks. Such peaks appear due to various reasons which are not essential, and hence are not suitable as peaks indicating the motion timings of the cardiac muscle. Therefore, a threshold is set to inhibit the detection of such peaks. This threshold can be changed by the operator as needed. The threshold setting function 72 may recognize this threshold and store it in a predetermined memory. Alternatively, a value stored in the apparatus in advance may be used. It has been confirmed by actual measurement that the concrete appropriate value of a threshold is 1 mm or less. If the input value exceeds the threshold, the flow advances to step S8. If the input value does not exceed the threshold, the flow advances to step S6.

In step S6, $\underline{t}$ is updated, and a peak search is continued at the new time point. If it is determined in step S7 that t<te, the search is terminated without detection of any valid peak. Otherwise, the flow returns to step S5.

In step S8, the first peak extraction function 71 determines whether the input value at time $\underline{t}$ is a peak. More specifically, the input value is time-differentiated. A time point at which this value is 0 or a time point at which the polarity of the differential coefficient changes is detected as a peak. If the value is a peak, tp1=t is stored as a peak candidate. The flow then advances to step S11. If the input value is not a peak, the flow advances to step S9.

In step S9, $\underline{t}$ is updated, and a peak search at the new time point is continued. If it is determined in step S10 that t<te, a larger one of the input values at times ts and te is detected as the first peak. If te≦t, the flow returns to step S5.

In step S11, $\underline{t}$ is updated. In step S12, it is determined whether the absolute value of the input value is smaller than a predetermined value. In this case, the predetermined value is the value obtained by multiplying an input value X at tp1 in step S8 by a value $\alpha$ set by the attenuation threshold setting function 74. The value $\alpha$ can also be set by the operator. This value may be recognized by the attenuation threshold setting function 74 and stored in a predetermined memory, or a value stored in the apparatus in advance may be used. It has been confirmed by actual measurement that the concrete appropriate value of $\alpha$ is 0.5 to 0.8. If the input value is smaller than the predetermined value, an input value X at time tp1 is detected as the first peak. Otherwise, the flow advances to step S13.

If it is determined in step S13 whether the input value X at time $\underline{t}$ is a peak, and an input value X' at time $\underline{t}$ is larger than the input value at time tp1. If both the conditions are satisfied, the flow advances to step S14 to change the peak candidate, and the resultant value is stored as tp1=t. The flow returns to step S11. If it is determined in step S13 that the above two conditions are not satisfied, the flow advances to step S15. If t<te, the input value X at time tp1 is detected as the first peak. Otherwise, the flow returns to step S11.

In this manner, a peak search is sequentially performed from ts to te. Assume that a peak search is performed at each point in the two-dimensional distribution of the motion information obtained from the motion information processing unit 6. In this manner, the two-dimensional distribution information of first peak arrival times is obtained.

In step S16, the color image generation function 82 converts the two-dimensional distribution information of the first peak arrival times into color information in accordance with the settings made by the color map setting function 81, and causes the display device 9 to display the resultant information. In this manner, the two-dimensional distribution information of the first peak arrival times is clearly presented to the operator.

Although not described above in particular, such operation may be sequentially performed for data received in real time, or an image obtained by past imaging operation may be called out and processed. If an image obtained by past imaging operation is to be called out, the step of calling out a past image is added before step S1, and the images sensed by the ultrasonic probe in step S3 are selectively discarded. In this case, the display control unit 8 may generate a still image by performing the above processing for a desired heartbeat designated by the operator.

When real-time processing is to be performed, the operation from step S4 to step S16 is repeated for each heartbeat. With this operation, an image is updated for each heartbeat. In addition, display processing may be performed in step S16 after a peak search in the entire range from ts to te is complete. Every time one peak is detected, color information may be displayed at the corresponding position, and the display of all color information may be reset at the start of a new heartbeat. In the latter case, display is performed by repeating the mode of sequentially performing coloring from a portion where the first peak is reached early on a B mode image on which color information is reset at the leading edge of a QRS wave.

A method of converting the first peak time into color information, which is performed by the color map setting function 81, will be described in detail below. This conversion is performed in accordance with the color map set by the color map setting function 81. A color map is a setting which indicates which color is assigned to which peak time, thereby assigning color information to each time point to create gradation like green→red gradation. Such information may be manually set by the operator or automatically set by the apparatus.

Although the above description has exemplified the color map for creating green→red gradation, it suffices if a color map using multiple colors can be selected. First of all, when a two-color map is to be used, color assignment is preferably performed such that green is assigned to indicate normal contraction and red is assigned to indicate a delay. In contrast to this, when a three-color map is to be used, abnormal premature contraction may be expressed by blue, normal contract may be expressed by green, and a delay may be expressed by red.

As a concrete automatic setting technique performed by the apparatus, a technique may be used, which sets a predetermined numerical value by using an electrocardiographic waveform such that, for example, a color changes at the time point corresponding to 600 ms from a QRS wave. In this embodiment, however, the systolic phase estimation unit 11 automatically detects a end-systolic phase, and the color map setting function 81 performs setting with reference to the detected phase.

The operation of the systolic phase estimation unit 11 will be described next. As a concrete example of automatic detection of a end-systolic phase, the technique disclosed in Jpn. Pat. Appln. KOKAI Publication No. 2004-161794 can be applied. This is a method of estimating a end-systolic phase in consideration of variations in heart rate based on cases of able-bodied people.

Severe heart failure cases often differ in end-systolic phase from cases of able-bodied people. In this embodiment, therefore, a end-systolic phase or a delayed systolic phase is estimated for every heartbeat. In a concrete example of estimating a end-systolic phase or a delayed systolic phase, one of the following four processes is performed for a predetermined area at a heartbeat immediately before observation: 1. obtaining the barycentric time of motion information at each point and obtaining an average barycentric time at the entire cardiac muscle by averaging the obtained barycentric times within the area, 2. averaging the pieces of motion information concerning displacements or strains in the area, obtaining the barycentric time of the average motion information, and obtaining an average barycentric time at the entire cardiac muscle, 3. obtaining the peak of motion information at each point, and obtaining an average peak time at the entire cardiac muscle by averaging the peaks, and 4. averaging the pieces of motion information concerning displacements or strains in the area, obtaining the peak of the average motion information, and obtaining an average peak time at the entire cardiac muscle.

The operator may be allowed to select any one of these processes.

The end-systolic phase or delayed systolic phase estimated in this manner is reflected in a color map at a heartbeat to be observed. More specifically, a predetermined range with reference to the estimated end-systolic phase may be set as a color map range. Alternatively, a delayed systolic time amount may be estimated by obtaining the variance of motion average time information within the area, and a color map may be determined with reference to the estimated amount.

(Display)

Figure 8:
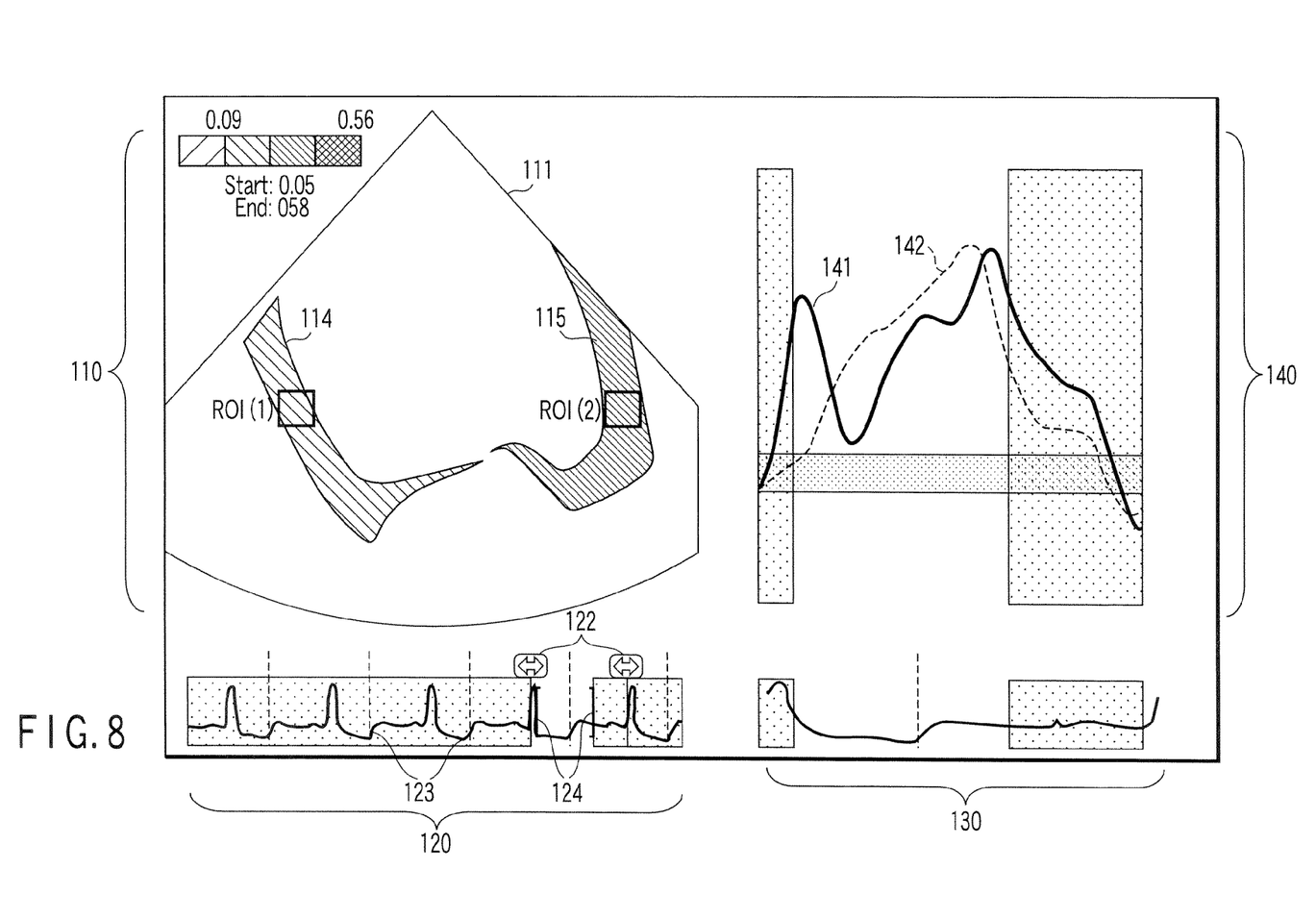
FIG. 8 is a view showing an example of an image generated by a display control unit in the embodiment in FIG. 1.

The function of this embodiment will be described next with reference to a concrete display example. FIG. 8 is a view showing a display example in this embodiment. The display control unit 8 causes the display device 9 to display a color image portion 110, an overall electrocardiographic waveform portion 120, an electrocardiographic waveform portion 130 in a designated area, and a temporal graph portion 140 of motion information.

The color image generation function 82 generates the color image portion 110 indicating a color morphological image 111 to be displayed with the first peak arrival time being superimposed as color information on a B mode image of the subject. The color image portion 110 indicates a time computation range 112 set by the computation range setting function 73. FIG. 8 shows a case wherein ts=0.05 and te=0.58 are set while the display time domain of the electrocardiographic waveform portion 130 of the designated area and the temporal graph portion 140 of motion information is defined as 1. In addition, the color map set by the color map setting function 81 is indicated by a color bar 113. In the case shown in FIG. 8, color information is assigned within the range of 0.09 sec to 0.56 sec from the start point of the display time domain. Referring to FIG. 8, for the sake of convenience, color information is substituted by density levels. In practice, however, the color information of gradation such as green→red gradation is assigned. In this display example, a long axis image of the left ventricle is displayed, and an abnormal premature contraction is occurring on a septum side 114. Therefore, the density of the shading on the septum side 114 is lower than that on a side wall side 115 on which a delay is occurring.

The electrocardiogram generation function 84 generates the overall electrocardiographic waveform portion 120 and the electrocardiographic waveform portion 130 of the designated area which are obtained from the electrocardiogram signal from the subject which is obtained by the electrocardiogram unit (not shown). A range to be displayed may be the entire range of selected image information or may correspond to several heartbeats with reference to a time point corresponding to the B mode image displayed on the color image portion 110. The operator sets at which heartbeat evaluation is to be performed by referring to the electrocardiographic waveform portion 120. One of the following concrete setting methods may be used: a method of allowing the operator to manually set a heartbeat by moving a cursor 122, and a method of automatically recognizing a heartbeat with reference to the leading edge of a QRS wave defined by a general electrocardiographic waveform. In addition, the areas indicated by the horizontal undulating lines are located outside a time computation range. A end-systolic phase 123 is displayed in the overall electrocardiographic waveform portion 120. The operator can set an appropriate display time domain by moving the cursor 122 such that sufficient portions before and after the end-systolic phase 123 are included.

A reference time point 124 on the color map is displayed on the overall electrocardiographic waveform portion 120. In accordance with the reference time point 124, a color map is assigned to each time point so as to create gradation like green→red gradation. As described above, in the case shown in FIG. 8, color information is assigned throughout the range from 0.09 sec to 0.56 sec. This setting may be manually made by the operator or automatically made by the apparatus. As a concrete automatic setting technique, one of the following methods may be used: a method of setting a predetermined numerical value in advance by using an electrocardiographic waveform, e.g., 600 msec after a QRS wave, and a method of setting with reference to the end-systolic phase 123 described above.

The electrocardiographic waveform portion 130 of the designated area is an enlarged display of an electrocardiographic waveform in correspondence with the display time domain designated by using the overall electrocardiographic waveform portion 120. The electrocardiographic waveform portion 130 of the designated area is displayed so as to be compared with the temporal graph portion 140 of the motion information.

The temporal graph generation function 83 generates the temporal graph portion 140 of the motion information which is a graph indicating a change in motion information with time in an ROI 114 designed on the color image portion 110 by the operator. Since the operator can grasp an abnormal region in a systolic phase by referring to the color image portion 110, he/she designates an arbitrary ROI while guiding the color image portion 110, and can analyze a change in local motion information with time. In the case shown in FIG. 8, the motion information of the ROI 1 is indicated by a solid line 141, and the motion information of the ROI 2 is indicated by a broken line 142.

Figure 9:
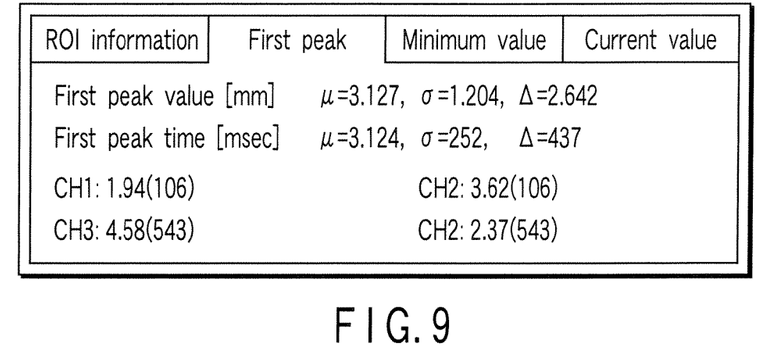
FIG. 9 is a view showing an example of an image indicating computation/analysis results generated by the display control unit in the embodiment in FIG. 1.

The display control unit 8 may also display analysis values concerning a change in local motion information with time which is designated by such an ROI. FIG. 9 shows an example of displaying such analysis values in the form of a table. Referring to FIG. 9, CH1 to CH4 correspond to ROIs designated by the operator. In this display example, four ROIs (CHs) are designated. The numerical value of each CH indicates the value (mm) of the first peak in each region, and the numeral enclosed with the parentheses indicates the arrival time (msec) of the first peak. In the field for the first peak values on the first row, the statistics of the first peak values of CH 1 to CH 4 are displayed. Referring to FIG. 9, reference symbol μ denotes an average value; σ, a standard deviation; and Δ, the difference between maximum and minimum values. In the field for the first peak times on the second row, the statistics of the first peak arrival times of CH 1 to CH 4 are displayed. Likewise, reference symbol μ denotes an average value; σ, a standard deviation; and Δ, the difference between maximum and minimum values.

In the temporal graph portion 140, regions outside the time computation range set by the computation range setting function 73 are mask-displayed in the horizontal undulating line areas, and the threshold set by the threshold setting function is mask-displayed in the dot area. The operator can set a time computation range and a threshold while referring to these areas. In the case shown in FIG. 8, motion information having positive polarity is a computation target. However, the present invention is not limited to this. When computation is to be performed for motion information with negative polarity, mask display is to be performed in an area on the negative side. Mask display is not limited to area display like that shown in FIG. 8. A broken line or a solid line may be displayed at a position corresponding to a threshold, and an arrow may be displayed at a position corresponding to a threshold on a value axis of a graph.

(Effect)

The effects of this embodiment will be presented below. According to this embodiment, a motion amount such as the displacement or strain of the cardiac muscle is detected, and a change in this motion amount with time is computed/analyzed. Since a displacement or a strain is a physical quantity obtained through time integration, a change with time is relatively stable as compared with the case wherein velocity is used as shown in FIGS. 12 and 13. According to this embodiment, therefore, the peak of motion information indicating abnormal contraction of the heart can be reliably detected as compared with a conventional technique like that disclosed in patent reference 1 which computes/analyzes a motion velocity.

In addition, according to this embodiment, the first peak arrival time of motion information is converted into color information and superimposed on a B mode image. Even if, therefore, the peak of motion information indicating abnormal contraction is smaller than a peak that appears upon the overall movement due to subsequent contraction, a time point indicating abnormal contraction can be detected as a peak. Therefore, abnormal contraction in early-systole in a severe heart failure case can be stably and easily grasped. Since it can be accurately determined whether systolic dyssynchrony is occurring, a patient for which the cardiac resynchronization therapy is effective can be accurately determined. That is, since unnecessary application of a therapy which exhibits a slight effect to a patient can be avoided, the burden on the patient or operator can be greatly reduced.

Figure 10:
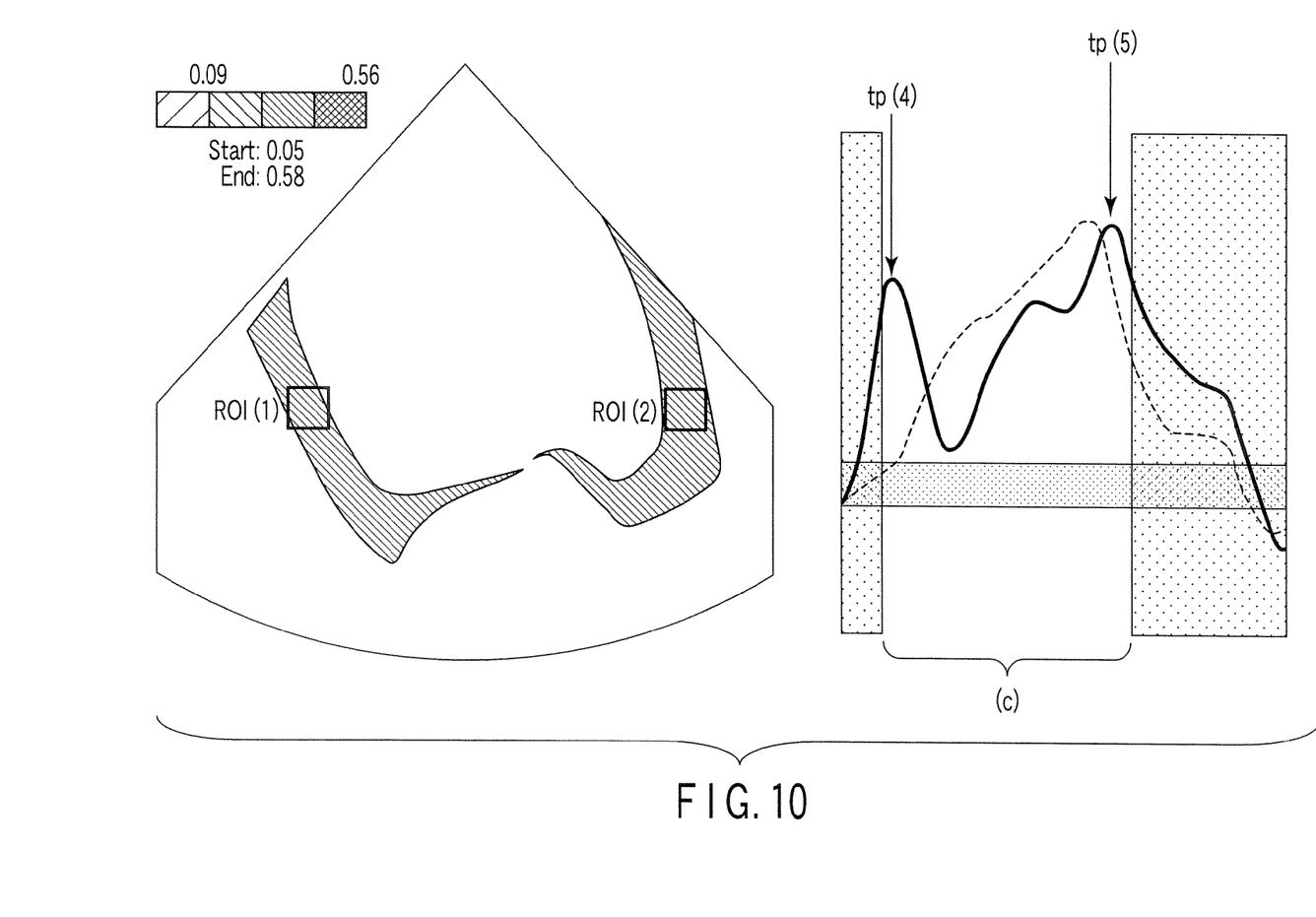
FIG. 10 is a view for explaining an effect obtained by a first peak extraction function in the embodiment in FIG. 1.

This relationship will be concretely described below with reference to FIG. 10. The displacements of the respective regions in one cardiac cycle are expressed in a graph with ROIs 1 and 2 on an ultrasonic image of a portion near the left ventricle being made to correspond to the solid line and the dotted line, respectively. In this case, when peak detection is performed in an area (C) including a early-systole interval, the peak of a curve indicating the displacement of the ROI 1 at the early-systole position indicated by tp4 is a peak indicating an abnormal behavior. Since this curve also has a peak at a position tp5 which appears in end-systole due to the overall movement, when peak detection is mechanically performed, the position tp5 indicating a higher displacement is detected as a peak. Since the peak at tp5 coincides with the position of the peak of the displacement of the ROI 2, it is detected that both the curves have peaks at the same time point. That is, the obtained analysis result indicates as if the regions ROI 1 and ROI 2 synchronously contract. In contrast to this, in the case shown in FIG. 8, in this embodiment, it can be recognized at a glance that the abnormal premature contraction occurring on the septum side can be reliably detected, and that the septum side contracts earlier than the side wall side on which a delay is occurring, and contraction asynchrony is occurring between the left ventricular walls.

In addition, in this embodiment, time computation is performed for only the input value of motion information which exceeds a predetermined threshold, and a relatively small peak of motion information is not detected as the first peak. Such peaks appear due to various reasons which are not essential, and hence are not suitable as peaks indicating the motion timings of the cardiac muscle. In this embodiment, therefore, the peak of motion information which indicates abnormal contraction of the heart can be reliably detected.

In addition, since motion information with a small value is also generally detected in the heart chamber, if such a threshold is not set, a peak is detected also in the heart chamber, and color information is superimposed. However, such information is unnecessary for the determination of systolic dyssynchrony and becomes a hindrance to observation. According to this embodiment, providing a threshold for input values to be computed makes it possible to detect the peak of motion information of the cardiac wall, on which relatively large motion information is detected, as the center. Therefore, an image having color information superimposed on only the cardiac muscle can be displayed. This facilitates the determination of the function of the cardiac muscle.

When a strain is used as motion information, since a strain is influenced by speckle noise more easily than a displacement, a change in strain with time often includes small peaks. According to this embodiment, however, providing a threshold for input values to be computed makes it possible to detect a strain due to the contraction of the cardiac muscle which appears as relatively large motion information. According to the embodiment, therefore, the peak of motion information which indicates abnormal contraction of the heart can be reliably detected.

Furthermore, for the above optimization of a threshold level, it is effective to set an optimal threshold for noise elimination by referring to a temporal graph of motion information like that shown in FIG. 8. According to this embodiment, as indicated by the dot area in FIG. 8, the range outside the computation target is mask-displayed by being superimposed on the graph on the basis of the threshold. Therefore, the operator can intuitively grasp an optimal threshold.

Figure 11:
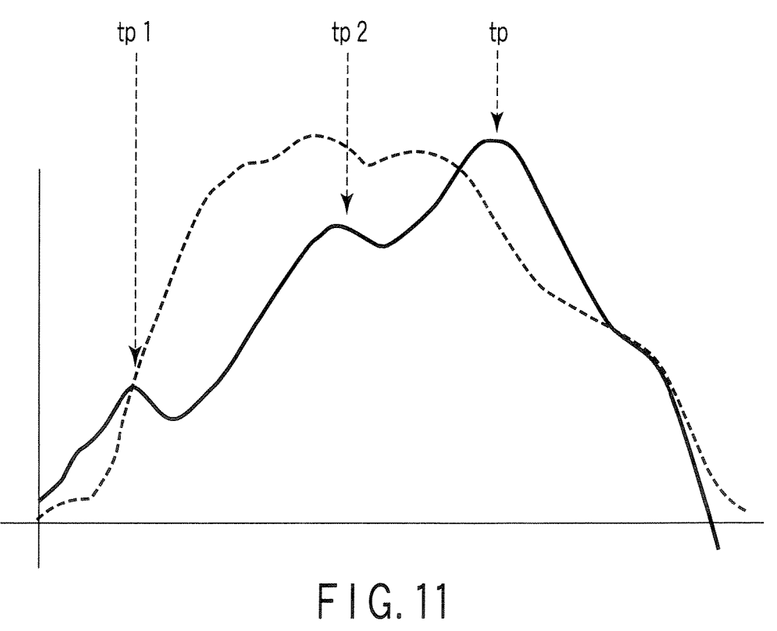
FIG. 11 is a view for explaining an effect obtained by an attenuation threshold setting function in the embodiment in FIG. 1.

According to this embodiment, an attenuation threshold can be set. In a heart failure case, the motion of the cardiac wall often includes irregular movement, and hence a peak does not always appear at end-systole of the cardiac muscle region. As shown in FIG. 11, in some case, peaks appear at three positions. However, in the case shown in FIG. 11, end-systole coincides with the time point corresponding to third time tp. In contrast, in the embodiment, after peaks are detected, only a peak whose value monotonously decreases to a value based on an attenuation threshold is extracted. This makes it possible to detect only a clear peak indicating abnormal contraction of the heart without extracting any unclear peaks.

In addition, according to this embodiment, a time computation range can be set. In computation using a short axis image, a peak often appears immediately after the leading edge of a QRS wave due to a rotation component in an isovolumetric contraction. According to the embodiment, however, setting a time computation range makes it possible to exclude such an area from a computation target. According to the embodiment, therefore, the peak of motion information indicating abnormal contraction of the heart can be reliably detected.

For the above optimization of a time computation range, it is effective to make optimal settings by referring to the temporal graph portion 140 of motion information like that shown in FIG. 8. According to this embodiment, as indicated by the dot area in FIG. 8, the range outside the computation target is mask-displayed by being superimposed on the graph. The operator can therefore intuitively grasp an optimal time computation range.

In addition, according to this embodiment, a end-systolic phase or a systolic delay phase is automatically estimated and reflected in a color map. This makes it possible to set a proper color map without bothering the user to set it, thereby reducing the burden on the operator. Furthermore, in the embodiment, a end-systolic phase or delayed systolic phase at a next heartbeat is estimated from motion information at a past heartbeat, and is reflected in a color map. Therefore, there is no need to set a color map after the end of imaging operation corresponding to one heartbeat. That is, a proper color map can be set at each heartbeat in real time. This facilitates continuous observation at many heartbeats and comprehension of the motion state of the subject.

Furthermore, according to this embodiment, a color map can be set by using two colors or three or more colors. Using a two-color map makes it possible to display information while enhancing only abnormal premature contraction. At the same time, using a three-color map makes it possible to comprehend at a glance both an abnormal premature contraction and an abnormal delay contraction. Therefore, an image in a proper display form can be acquired in accordance with the purpose of diagnosis or the state of a subject. According to the embodiment, therefore, the burden on the operator in diagnosis can be reduced.

(Modification)

Obviously, the present invention is not limited to the above embodiment, and can be variously modified within the spirit and scope of the invention.

For example, a technique of applying a load to a subject by means of motion or a drug and color-displaying peak arrival times before and after the application has been proposed by the present inventors in a Japanese Patent Application (Patent Application No. 2004-210110). This technique may be applied to the present invention so as to use at least one of the first peak extraction function, threshold setting function, computation range setting function, and attenuation threshold setting function for comparison between motion states before and after the above application of a load. This also makes it possible to obtain the same effects as those of the embodiment described above.

In this embodiment, the first peak extraction function, threshold setting function, computation range setting function, and attenuation threshold setting function are used for the analysis of motion information concerning a strain or displacement. However, the present invention is not limited to this. These functions can be applied to motion information concerning a velocity, variance, and power value.

This embodiment comprises the first peak extraction function, threshold setting function, computation range setting function, attenuation threshold setting function, and systolic phase estimation unit. However, the embodiment need not comprise all of them. Obviously, with a combination including at least one of them, a corresponding effect of the effects of the above embodiment can be obtained.

The above embodiment has exemplified the case wherein a reception signal is obtained in a two-dimensional space. However, the present invention is not limited to this. Assume that a reception signal representing a plurality of two-dimensional slices has been obtained, a reception signal has been obtained in a three-dimensional space, or a feature amount is obtained from a three-dimensional space and the computation result is projected/displayed on a two-dimensional plane as in the case of a polar-map. The present invention can be applied to such a case by the expansion or conversion of the dimensions in the above embodiment.

This embodiment has described the process from the acquisition of a reception signal from the ultrasonic probe to display operation on the display device. However, the present invention is not limited to this. The characteristic components of this embodiment are the motion information computation unit, time computation unit, display control unit, and systolic phase estimation unit. The present invention can therefore be applied to an apparatus which includes at least one of these components and processes external information. More specifically, the present invention may be applied to an ultrasonic image processing apparatus which performs processing by using a computer such as a PC or workstation independently of an ultrasonic diagnostic apparatus.

Note that the present invention is not exactly limited to the above embodiments, and constituent elements can be modified and embodied in the execution stage without departing from the spirit and scope of the invention. In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

What is claimed is:

1. An ultrasonic image processing method, comprising:
   acquiring motion information of a tissue at a plurality of positions in a subject to be examined, the motion information of the tissue being obtained by a calculation of time integration of a velocity of the tissue;
   detecting extreme values of a change in the motion information of the tissue with time in a predetermined time range, and extracting a first extreme value that exceeds a predetermined threshold;
   detecting a time taken to reach the first extreme value from an arbitrary time point as a motion timing of the subject; and generating a first image indicating information associated with the motion timing.

2. An ultrasonic image processing apparatus, comprising:
a motion information computation unit which acquires motion information of a tissue at a plurality of positions in a subject to be examined, the motion information of the tissue being obtained by a calculation of time integration of a velocity of the tissue;
a time computation unit which detects extreme values of a change in the motion information of the tissue with time in a predetermined time range, and extracts a first extreme value that exceeds a predetermined threshold, and detects a time taken to reach the first extreme value from an arbitrary time point as a motion timing of the subject; and
a display control unit which generates a first image indicating information associated with the motion timing.

3. An apparatus according to claim 1, wherein the motion information is a quantitative value associated with a strain of the tissue of the subject or a quantitative value associated with a displacement of the subject.

4. An apparatus according to claim 1, wherein the time computation unit detects at least one of an extreme value of a change in the motion information with time in a predetermined time range, a point at which a predetermined threshold is reached, and a center of gravity, as a feature point, and acquires a time taken to reach the feature point from an arbitrary time point as the motion timing.

5. An apparatus according to claim 4, wherein the display control unit generates an image indicating analysis values or statistics associated with said plurality of feature points.

6. An apparatus according to claim 1, wherein the time computation unit extracts a candidate for the first extreme value by sequentially searching for a extreme value of the motion information from an old time point to a new time point in the predetermined time range, sets, as an attenuation threshold, a value obtained by multiplying a value of motion information at a time point at which a candidate for the first extreme value is extracted by a numerical value less than one, and extracts the candidate for the first extreme value as the first extreme value when a value of motion information of the tissue becomes smaller than the attenuation threshold in a time range which falls within the predetermined time range and is newer than the candidate for the first extreme value.

7. An apparatus according to claim 1, which further comprises a threshold setting unit which sets the predetermined threshold, wherein
the time computation unit detects the motion timing by using motion information of the tissue which has a value larger than the set predetermined threshold.

8. An apparatus according to claim 7, wherein the threshold setting unit changes the threshold in accordance with an input from an operator.

9. An apparatus according to claim 1, wherein the display control unit generates an image representing a two-dimensional distribution or three-dimensional distribution of the motion timing.

10. An apparatus according to claim 9, wherein the display control unit generates an image obtained by superimposing a color corresponding to the motion timing on a B mode image at a corresponding position.

11. An apparatus according to claim 1, wherein the display control unit generates a second image including a temporal change curve of motion information at least one position of the motion information of the tissue at a plurality of positions, and a range of a threshold set on the temporal change curve.

12. An apparatus according to claim 1, wherein the display control unit generates a third image indicating a temporal change curve of motion information at least one position of the motion information of the tissue at a plurality of positions, and a predetermined time range set on the temporal change curve.

13. An apparatus according to claim 12, wherein the predetermined time range is set in accordance with an input from an operator.

14. An apparatus according to claim 1, wherein the display control unit generates the first image to which different colors are assigned in accordance with an abnormally early motion timing and an abnormally late motion timing such that the motion timings are configured to be discriminated.

15. An apparatus according to claim 1, wherein the display control unit generates the first image to which different colors are assigned in accordance with an abnormally early motion timing, a normal motion timing, and an abnormally late motion timing such that the motion timings are configured to be discriminated.

16. An apparatus according to claim 1, wherein the display control unit detects information associated with a motion state in the subject from the motion information, and generates the first image to which different colors are assigned in accordance with motion timings on the basis of the information associated with the motion state.

17. An apparatus according to claim 1, which further comprises an estimation unit which estimates a telesystolic phase at a current heartbeat of the heart in the subject or a delay phase after telesystole on the basis of the past motion information, and in which
the display control unit generates the first image which is an image for displaying the estimated time phase on an electrocardiographic waveform, and to which different colors are assigned in accordance with the motion timings in response to designation by an operator with respect to the electrocardiographic waveform.

18. An apparatus according to claim 1, which further comprises an estimation unit which estimates a telesystolic phase at a current heartbeat of the heart in the subject or a delay phase after telesystole on the basis of the past motion information, and in which
the display control unit generates the first image which is an image for displaying the estimated time phase on an electrocardiographic waveform, and to which different colors are assigned in accordance with the motion timings in response to designation by an operator.

19. An apparatus according to claim 1, wherein the motion information computation unit tracks motion of the tissue in the subject and acquires the motion information on the basis of a change in the velocity of the subject with time in accordance with the tracking.

20. An apparatus according to claim 1, wherein the motion information computation unit performs angle correction for the motion information in accordance with a position or shape of the subject.

* * * * *